United States Patent [19]
Lafontaine

[11] Patent Number: 5,964,714
[45] Date of Patent: Oct. 12, 1999

[54] PRESSURE SENSING GUIDE WIRE

[75] Inventor: Daniel M. Lafontaine, Plymouth, Minn.

[73] Assignee: Scimed Life Systems, Inc., Maple Grove, Minn.

[21] Appl. No.: 08/614,774

[22] Filed: Mar. 7, 1996

[51] Int. Cl.[6] .................................................. A61B 5/00
[52] U.S. Cl. ........................................... 600/561; 600/585
[58] Field of Search .................................. 600/585, 561, 600/587, 595

[56] References Cited

U.S. PATENT DOCUMENTS

| | | |
|---|---|---|
| 4,909,796 | 3/1990 | Hagio et al. . |
| 5,065,769 | 11/1991 | de Toledo . |
| 5,113,868 | 5/1992 | Wise et al. ............................ 600/986 |
| 5,184,627 | 2/1993 | de Toledo . |
| 5,211,636 | 5/1993 | Mische . |
| 5,284,138 | 2/1994 | Kujawski ............................. 600/478 |
| 5,322,508 | 6/1994 | Viera . |
| 5,450,853 | 9/1995 | Hastings et al. . |
| 5,476,450 | 12/1995 | Ruggio . |
| 5,569,197 | 10/1996 | Helmus et al. . |
| 5,573,007 | 11/1996 | Bobo, Sr. . |

OTHER PUBLICATIONS

New Product Bulletin, Medi–Tech, Cragg Convertible Wire, Mar. 1989.

Products for Regional Thrombolysis, Medi–Tech, Katzeen Infusion Wire, Mewissen Infusion Catheter, Cragg Convertible Wire, Jul. 1992.

The Sos Open Ended Guidewire from USCI, Applications & Case Studies, C.R. Bard, Inc., Nov. 1985.

*McDonald's Blood Flow in Arteries, theoretical, experimental and clinical principles*, Third Edition, Wilmer W. Nichols and Michael F. O'Rourke, Chapter 6 —Measuring Principles of Arterial Waves, pp. 143–162. 1990 (London).

*Diagnostic and Therapeutic Cardiac Catheterization*, Carl J. Pepine, M.D., et. al., Chapter 18 —Pressure Measurement, pp. 283–297. 1989.

*Primary Examiner*—Cary O'Connor
*Assistant Examiner*—Pamela Wingood
*Attorney, Agent, or Firm*—Todd P. Messal

[57] ABSTRACT

A guide wire that is capable of sensing pressure at its distal. The guide wire contains a non-compliant path from its distal end to a pressure transducer, at its proximal end, that has a maximum signal rating of 10–1,000 times the nominal signal.

9 Claims, 6 Drawing Sheets

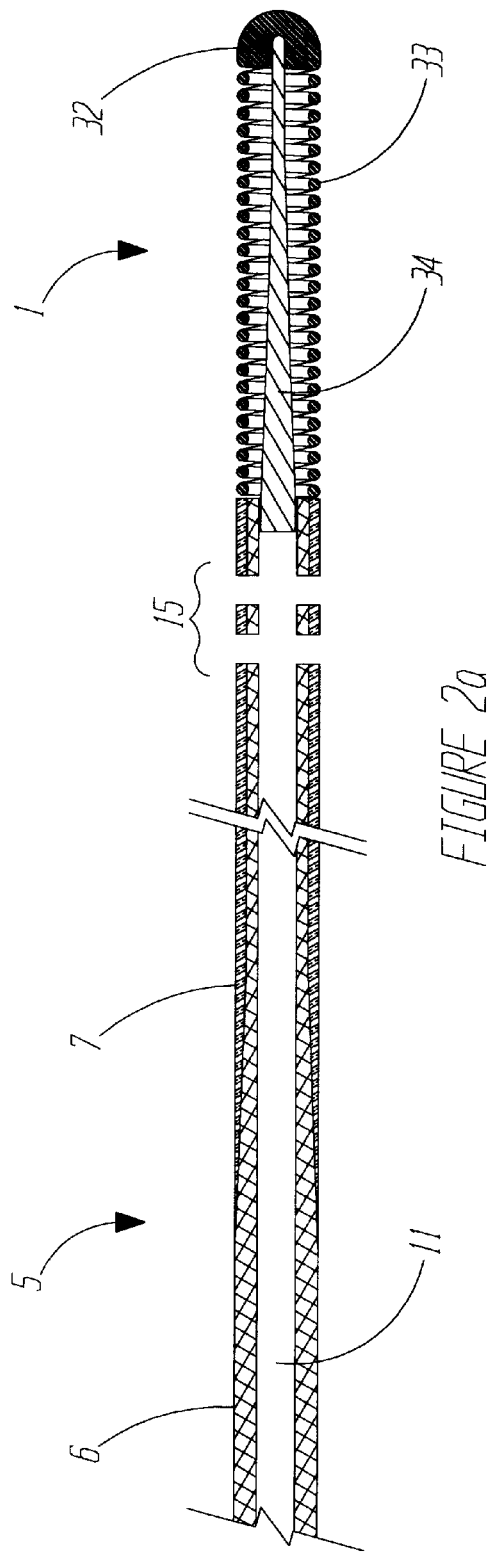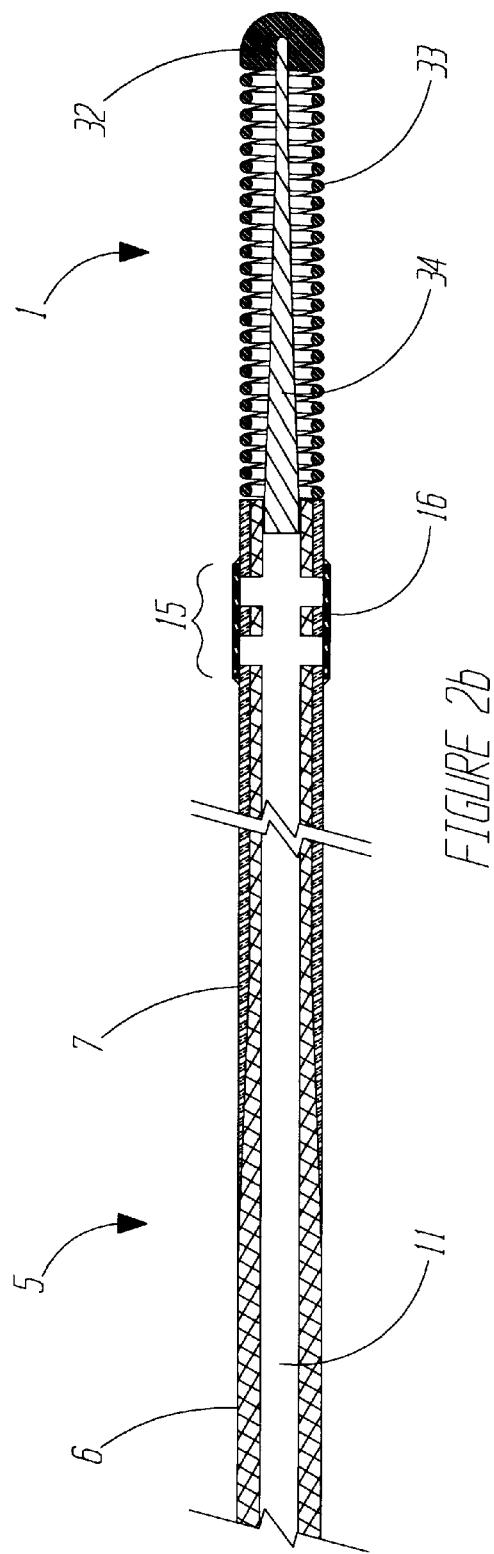

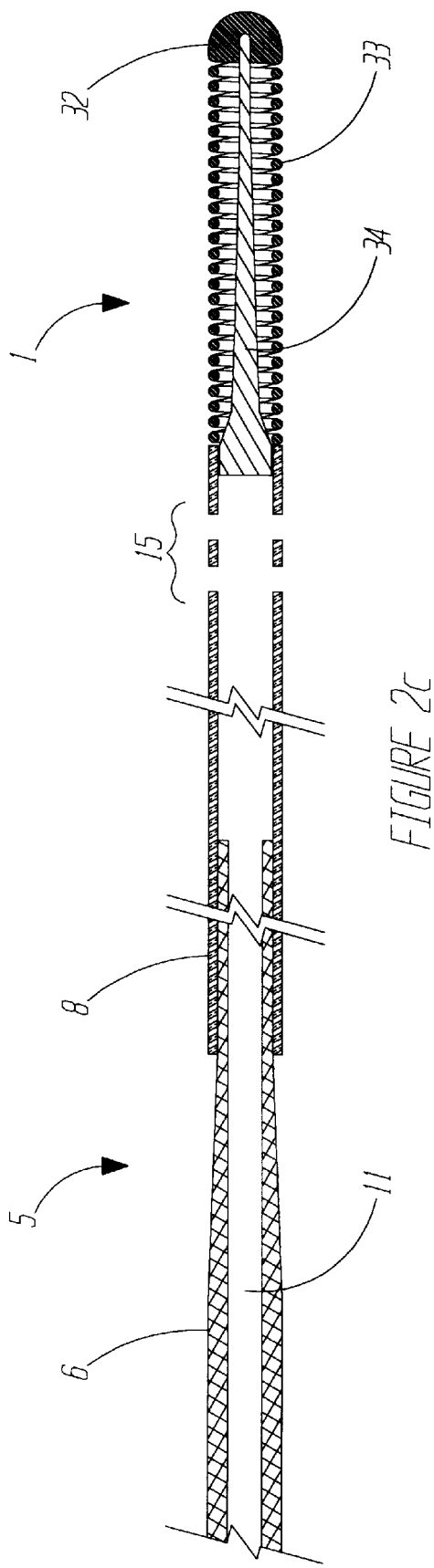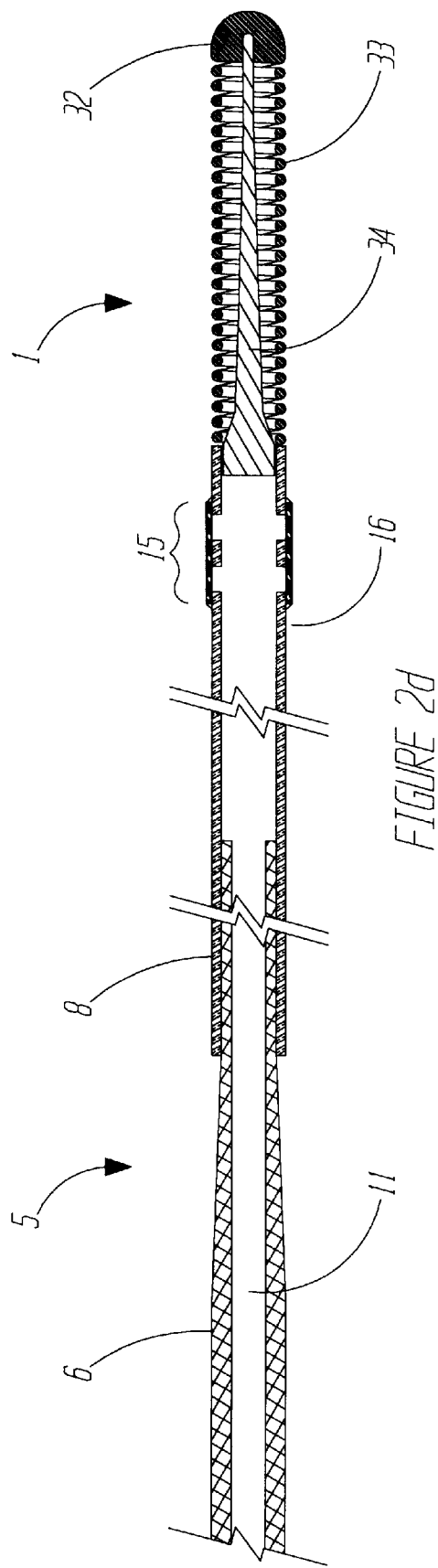

PRESSURE SENSING GUIDE WIRE

FIELD OF THE INVENTION

The invention relates to a pressure sensor, and more particularly, a wire capable of functioning as a guidewire and measuring fluid pressure at various places within the human vasculature.

BACKGROUND OF THE INVENTION

Angioplasty procedures have gained wide acceptance in recent years as efficient and effective methods for treating types of vascular disease. In particular, angioplasty is widely used for opening stenoses in the coronary arteries although it is also used for the treatment of stenoses in other parts of the vascular system.

The most widely used form of angioplasty makes use of a dilation catheter which is threaded over a guidewire and has an inflatable balloon at its distal end. Inflation of the balloon at the site of the occlusion causes a widening of the lumen to reestablish an acceptable blood flow through the lumen.

Often it is desirable to determine the severity of the occlusion in order to properly choose a dilation catheter. Various invasive techniques have been used to determine the severity of the occlusion. One way of determining the severity of the occlusion is to measure pressure both proximal to and distal of the stenoses. Devices that are used for this purpose include catheter-like members with some type of pressure sensing device incorporated therein. For devices of the single pressure sensor type, movement of the catheter-like member must be accomplished to measure pressure at different locations. Whereas, devices with more than one pressure sensor can measure pressure simultaneously at several points.

One known device measures the pressure as a function of the deflection of a diaphragm located at the distal end of the catheter. Positioning the sensing part of the sensing device at the distal end of the catheter requires the sensing device to be made extremely small. Otherwise, the sensing device will impede blood flow and effect the pressure reading. In addition, catheters with the sensing device at the distal end do not allow for reuse of the expensive sensing device.

Another known device, called a fluid filled catheter-manometer, connects a sensing device to the proximal end of the catheter. A catheter-manometer uses a fluid column that can communicate pressure changes at the distal end of the device to a transducer located at the proximal end of the device. A catheter-manometer has the advantage of having a reusable sensor and is therefore less expensive. Unfortunately, catheter-manometers have heretofore not been accurate at physiologic frequencies. The required bandwidth, or flat frequency response, for accurate physiologic pressure measurement in the heart about 30 hertz. Large catheter-manometers (8 Fr) are typically only 20 hertz and small catheter-manometers, like guidewire systems (0.014"), may be less than 1 hertz. Further the bandwidth of catheter tip pressure devices may be several kilohertz. Clearly, prior art catheter-manometer systems have not had the required bandwidth or frequency response for accurate physiologic pressure measurement.

There are several factors causing prior art catheter-manometer systems to not have the required bandwidth or frequency response for accurate physiologic pressure measurement. One factor is that a relatively large amount of fluid mass must be moved with a relatively small amount of pressure. The movement of the mass is described by Newton's second law of motion: F=Ma, where the force F is a combination of a displacing force and restoring force. The displacing force is the pressure input and the restoring force is the natural rebound response of the system. Therefore, the density of the fluid becomes a contributing factor to the frequency response.

Another factor is resistance R. The resistance to flow in a catheter can be described by Poiseuille's equation: $R=8\mu L/\pi r^4$, where r is the internal diameter and L the length of the catheter. In a fluid-filled manometer system the fluid is typically not flowing, but rather is oscillating, as originally described by Lambossy (1952). Thus, in a fluid filled manometer, the damping (resistance) varies as the square-root of the length and inversely as the cube of the radius as follows:

$$\beta = \frac{4\mu}{r^3} \sqrt{\left(\frac{pL}{\Delta E}\right)}.$$

Yet another factor is the compliance or elasticity E of the system. The catheter combined with the pressure transducer form an elastic volume in which the response is described by:

$$E = \frac{\Delta P}{\Delta E}.$$

Thus, the natural frequency response of the fluid filled catheter manometer will be determined by stiffness or compliance of all components in the system. Prior art systems are composed of the catheter, a manifold, tubing, fittings, and a transducer. Catheters are made of combinations of metals and plastics which may, depending on construction, have compliance which absorbs some of the pressure change. Manifolds are made of hard plastics which typically do not elastically deform. However, the tubing used is elastomeric, as are the gaskets used with the fittings. These elastomers are very flexible and will dampen pressure change in the fluid passing through them as described above.

Finally, the responsiveness of the pressure transducer within the sensing device is also a factor. As previously described, all components in the system contribute to the elasticity E, and thus the frequency response. In order to have adequate sensitivity in the physiologic pressure range (about 0–5 Psi), blood pressure transducers have traditionally been designed for full scale signal output (maximum pressure rating) at applied pressures of 300 mmHg or 5 Psi. The very flexible diaphragms used to create adequate low pressure sensitivity increases the elasticity of the system, and thus, lowers the frequency response. All of these factors have thus far contributed to making devices of this type less accurate in reproducing the exact physiologic signals and produce pressure readings which are, in some devices, only an average of a patient's blood pressure over time.

In addition to procedures like angioplasty where it is desirable to know the pressure at a given point at a given time, it is also highly desirable to know the pressure wave form for places within the heart and various vessels. Standard pressure wave forms have been documented for the healthy vasculature. A, variety of other wave forms have also been documented to correspond to particular maladies. Therefor, a device which was responsive enough to measure wave forms within the heart chambers would also be useful.

Tremulis discloses in U.S. Pat. No. 4,953,553, U.S. Pat. No. 4,964,409, and U.S. Pat. No. 5,050,606 guide wires capable of sensing pressure via a proximal sensing device. This device has the added advantage of being usable as a guidewire. Guide wires are commonly used during angioplasty as well as many other procedures. However, this device is not as sensitive as distal sensing devices because of all of the factors previously described nor does it have enough frequency response to measure accurate wave forms.

Accordingly, it is desirable to provide a device that can be used as a guidewire and simultaneously be used to measure pressure at specific points without the added expense of distal sensors and without the pressure change insensitivity of prior art proximal sensing devices. Further it would be highly desirable to combine this device with a device that could produce a true wave form of the changes in blood pressure as well as an average blood pressure measurement.

SUMMARY OF THE INVENTION

The present invention overcomes the deficiencies of the prior art by providing a pressure sensing medical device with a minimal fluid path, all noncompliant components, and a high pressure transducer that has a full scale signal output of 10–1,000 times physiologic pressure. In one embodiment of the invention the device has an elongate body consisting of at least two internal lumens extending from the proximal end of the device to the distal end of the device. Each lumen has a set of holes at the distal end of the device which allows fluid to flow from the distal end of the device to the proximal end of the device. These lumens make it possible for fluid pressure changes to be communicated from the distal end of the device to the proximal end. A connector having one or more ports is connected to the proximal end of the device and at least one of the ports is adapted to be fitted to a high pressure transducer.

In use the embodiment of this invention would be introduced into a patient's vasculature and advanced to a point where the distal-most set of holes is distal of a vascular lesion and the proximal-most set of holes is proximal of the lesion. Pressure can be measured then simultaneously on each side of the lesion and a pressure gradient can be determined or the ratio of distal to proximal pressure can be computed.

In a second embodiment of the invention, a metal hypotube is ground to a tapered section at the distal end. This tapered section is covered with a polymer to provide a more flexible distal section. Holes near the distal end allow fluid pressure to be communicated into the inner portion of the hypotube. The distal most end of the hypotube is connected to a standard guide wire spring tip. A noncompliant connector having one or more ports is connected to the proximal end of the hypotube and at least one of the ports is adapted to be fitted to a high maximum pressure rating transducer.

In a variation of the second embodiment of the invention, the tapered section of the hypotube is only partially covered by a second metal tube which extends distally of hypotube. Holes near the distal end of the second metal tube allow fluid pressure to be communicated into the inner portion of the hypotube. A spring tip is attached to the distal most end of the second metal tube.

In another variation of the second embodiment of the invention, the hypotube is filled with a fluid or a gel. The fluids may be added to the device just prior to the procedure or when the device is manufactured. Gels would have to be put into the device by the manufacturer and have the added benefits of not drying out or running out of the device.

Embodiments of the invention may also have a one way fluid valve and a two way pressure valve sealing each hole. These valves allow fluid and air to be forced out of the invention while maintaining the invention's ability to transfer pressure changes from the distal end to the proximal end of the invention.

In use the embodiments of the invention described above may be used in all of procedures that typically use a guidewire. At any point in the procedure the transducer may be attached to a display and the pressure and a wave form may be generated. Uses of this device may include diagnostics before and after angioplasty, on the proximal and distal sides of a lesion, and in specific locations in and around the heart, including the chambers of the heart for cardiac assessment, and across the heart valves for pressure gradients. Further, as guide wires these devices will be well suited for any physiologic pressure measurements including gastrointestinal, neurological, spinal, urological, respiratory and the peripheral vasculature.

BRIEF DESCRIPTION OF THE DRAWINGS

FIG. 1b is a side view of a membrane covering a hole in the device in FIG. 1a.

FIG. 1c is a side view of a second type of membrane covering a hole in the device in FIG. 1a.

FIG. 2a is a cross section of a second embodiment of the distal end of the device in FIG. 1a.

FIG. 2b is a cross section of a first variation of the embodiment shown in FIG. 2a.

FIG. 2c is a cross section of a second variation of the embodiment shown in FIG. 2a.

FIG. 2d is a cross section of third variation of the embodiment shown in FIG. 2a.

FIG. 3a is a side view of an embodiment of the connector assembly for use with the invention.

FIG. 3b is an end view of the embodiment of FIG. 3a.

DETAILED DESCRIPTION OF THE INVENTION

Figure 1A:
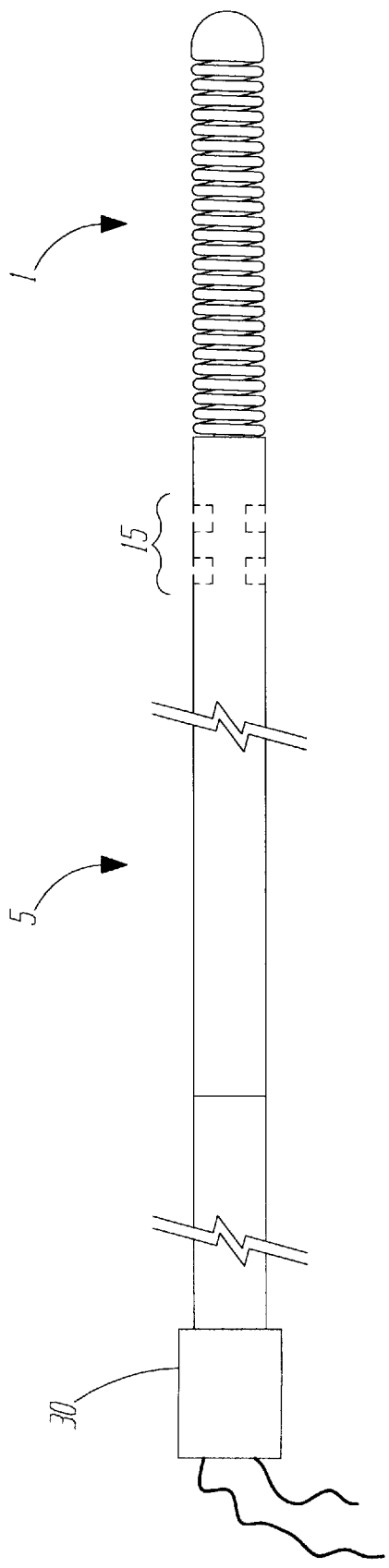
FIG. 1a is a side view of a first embodiment of the invention.

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions, and manufacturing process are provided for selected elements. All other elements employ that which is known to those skilled in the field of the invention. Those skilled in the art will recognize that many of the examples provided have suitable alternatives that may also be utilized.

As shown in FIGS. 1a–2d, a first embodiment of the invention depicts a guide wire having an elongate body 5 with proximal and distal ends and at least one lumen 11 therethrough. Each lumen 11 has a proximal opening corresponding to the proximal end of elongate body 5 and a distal opening corresponding to the distal end of elongate body 5. At the distal end of elongate body 5 an atraumnatic tip 1 is bonded to the distal opening of the lumen.

In FIGS. 2a–2d an example of an atraumatic tip 1 is shown where the atraumatic tip 1 is a spring tip. Spring tips are well known in the guide wire art and the following description discloses some but not all of the possible materials and methods of construction. A tapered shaft 34 is bonded at its proximal end into the distal opening of lumen 11. Shaft 34 may be welded, adhesively attached, or bonded to elongate body 5 in any way such that a fluid tight and pressure tight seal is formed. Shaft 34 is brazed to a coil 33 at its distal end to form a bead 32. Coil 33 may be made of a radio-opaque material such as, platinum-iridium alloy or other suitable medical grade radio-opaque alloy, to make the spring tip more visible under fluoroscopy. Coil 33 has a diameter of about 0.010–0.020" and encircles shaft 34 along its entire length. Coil 33 is further attached to shaft 34 by welding the proximal portion of coil 33 to the distal end of elongate body 5. Those skilled in the art will recognize that other atraumatic tips 1, such as a polymer covered tip, could be used with the present invention.

Elongate body 5 has holes 15 located near the distal end of elongate body 5. Holes 15 pierce elongate body 5 and make a complete fluid path from the exterior of the distal end of elongate body 5 via lumen 11 to the proximal end of elongate body 5. Holes 15 may be circular, oval, or slot-like and, in the preferred embodiment, each elongate body 5 has at least two and preferably 4 holes 15 in communicating with each lumen 11 therein.

In order to effectively communicate pressure from holes 15; along lumen 11 to the proximal end of elongate body 5, the entire fluid pathway must be so rigid as to be non-compliant, ie. the flexing of materials in contact with the fluid will not absorb any pressure changes. In addition, lumen 11 must be filled with a non-compliant fluid. Suitable fluids include water, heparin, ringers, fluids drugs, saline, silicone oil, gel, silicone gel, alcohol, or perfluorocarbon. These fluids can be pre-filled when the device is manufactured or injected into the device just prior to use. The material that surrounds lumen 11 must also be non-compliant. Suitable materials include Nitinol™, stainless steel, polycarbonate, or other non-compliant medical grade alloys, polymers, or composites. The resulting structure insures that a displacing force on the exterior of the distal end of elongate body 5 will cause a force equal to the displacing force to be communicated to the proximal end of elongate body 5 via the fluid in lumen 11.

Figure 1C:
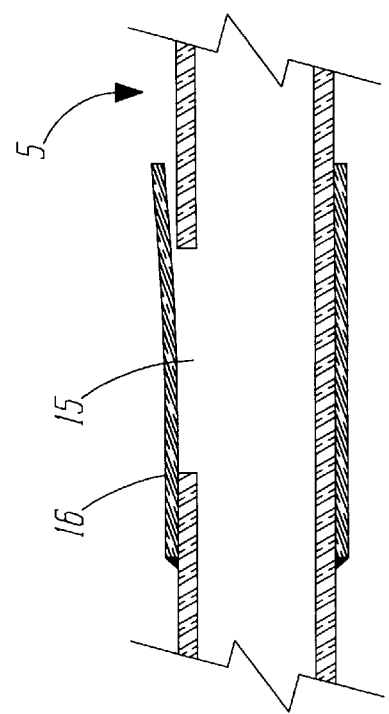
Figure 1B:
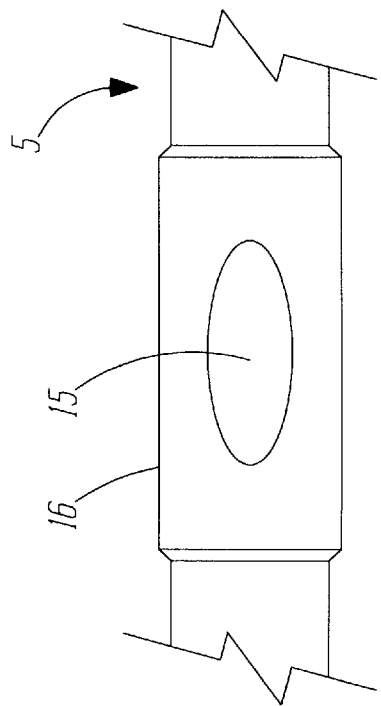

It is also preferable to have each hole 15 act as a one way fluid valve and a two way pressure valve, as shown in FIG. 1b and 1c. That is, each hole 15 may allow fluid, including fluid air, to pass only from the interior of elongate body 5 to the exterior while also allowing pressure to be communicated across the valve. This is preferably accomplished by surrounding the hole 15 with a PTFE membrane sleeve 16 as shown in FIG. 1b. One example of a material that may be used as the membrane sleeve 16 is Gortex™ with a maximum pore size of 4 microns. Gortex™ is constructed such that its pore structure allows fluid to pass through the membrane in only one direction. As a membrane though, a sleeve made of this material still communicates pressure in either direction. A sleeve of this or other suitable material may be placed over each hole 15 and bonded at each end of the sleeve. Further, a single sleeve may placed over several holes 15 and bonded on each side of each hole 15.

Alternatively, a membrane sleeve 16 may made be of an elastomer like urethane, a glass fiber composite, or an acrylic copolymer. Use of any of these materials would allow pressure to be communicated across the sleeve 16 but would not allow fluid to pass through the sleeve 16. This type of membrane sleeve 16 may be bonded to the elongate body 5 on only one side, preferably the proximal side, of hole 15 as shown in FIG. 1c. In this manner of construction, a positive pressure differential between the interior of elongate body 5 and the exterior of elongate body 5 would force any air and or other fluid out of the interior of elongate body 5 through the unbonded end of the membrane sleeve 16. When the pressure on the exterior of elongate body 5 is equal to or greater than that of the interior, the sleeve 16 would seal the hole 15 to any fluid flow. As an elastomer, sleeve 16 would continue to flex toward the lower pressure side of hole 15 and as such would allow pressure to pass through hole 15 without the transfer of fluid.

Referring back again to FIG. 1a, a high pressure transducer 30, preferably with a full scale pressure capability of 10–1,00 times normal blood pressure is sealingly connected and in fluid communication with lumen 11 in the proximal end of elongate body 5. Use of a high pressure transducer which has a very high signal to noise ratio allows physiologic pressure variations to be sensed with only a tiny displacement of the fluid column. Thus relatively rapid pressure variations are communicated accurately through the very small displacement of a small mass of fluid within a non-compliant system. An example of a high pressure transducer 30 may be a silicon piezoresistive pressure transducer, an example of which is the Lucas Nova™ sensor, NPC-102. Pressure transducer 30 preferably has a 1 mmHg sensitivity and a full scale pressure capability which, as previously described, is 10–1,000 times greater than the range of interest. Where, preferably the use of a 500 psi lull scale transducer with the invention has been found to provide good results for measuring blood pressure (approximately 5 psi).

In an alternative embodiment, a dual transducer system may be used to compensate for inaccuracies introduced by variations in the damping coefficient due to mechanical interface variations like air introduced into the system and mechanical tightness. A dual transducer system works by using two identical transducers 30 to create a reference pressure in one transducer 30 and a sensed pressure in the other transducer 30. The reference signal is then filtered to contain a DC or static pressure signal which is subtracted from the dynamic pressure signal. The difference is the offset connect pressure.

FIGS. 2a shows one approach to the construction of the distal end of the embodiment of FIG. 1a. In FIG. 2a, elongate body 5 is composed of a core member 6, having a lumen 11 therethrough and an traumatic tip 1 as previously described. Core member 6 may be made of Nitinol™ or any other suitable medical grade alloy and is preferably made of stainless steel. Core member 6 may be either standard guide wire length, about 150–175 cm, or standard exchangeable guide wire length, about 300 cm. At its proximal end core member 6 has an outer diameter of 0.014" and an inner diameter of 0.008". At the distal end of core member 6 the outer diameter of core member 6 tapers to 0.011". A suitable medical grade polymer 7 covers the tapered section of core member 6 making the elongate body have a uniform diameter along its entire length, e.g. 0.003" of polymer 7 surrounds the distal end of core member 6. Through the distal section of core member 6 are holes 15 which allow fluid communication between the interior and exterior of core member 6. As previously described, holes 15 may be covered by a membrane sleeve 16 as shown in FIG. 2b.

FIGS. 2c illustrates a second approach to the construction of the distal end of the embodiment of FIG. 1a. In FIG. 2c elongate body 5 is composed of a core member 6 and hypotube 8. Elongate body 5 has a lumen 11 therethrough and an atraumatic tip 1 as previously described. Core member 6 may be made of stainless steel or any other suitable medical grade alloy and is preferably made of Nitinoll™. Elongate body 5 may be either standard guide wire length, about 150–175 cm, or standard exchangeable guide wire length, about 300 cm. The distal end of core member 6 tapers to an outer diameter of 0.0105" and is suitable for insertion into hypotube 8. The distal end of core member 6 fits within hypotube 8 which has an outer diameter of 0.014" and an inner diameter of 0.0105". Core member 6 may be bonded or press fit together with hypotube 8 and may be made of any medical grade metal but is preferably Nitinol. Through the distal section of hypotube 8 are holes 15 which allow fluid communication between the interior and exterior of hypotube 8. As previously described, holes 15 may be covered by a membrane sleeve 16 as shown in FIG. 2d.

Figures 3A, 3B:
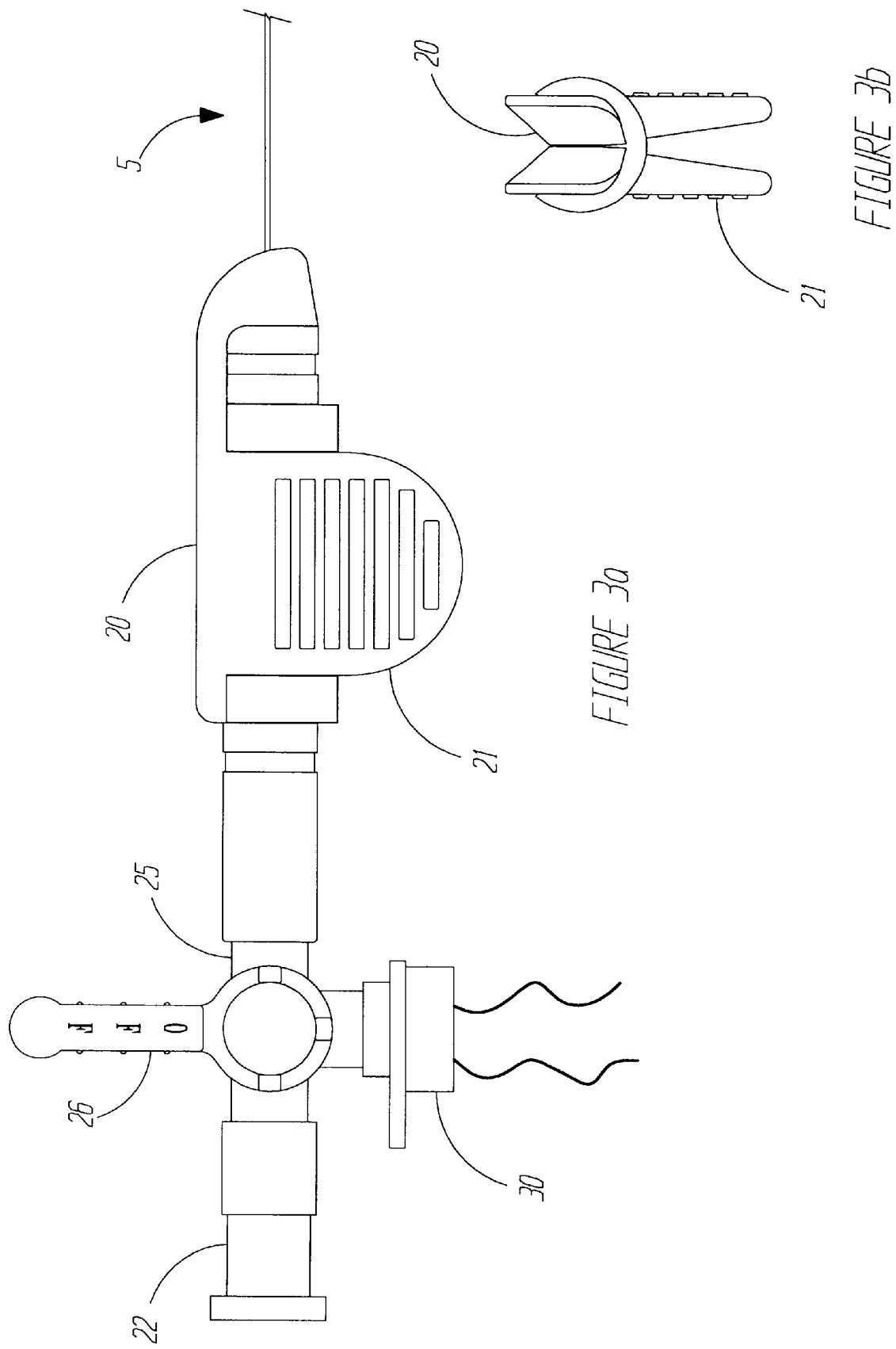

FIGS. 3a and 3b depict a method of connecting the proximal end of elongate body 5 to a pressure transducer 30. Gripper 20 is a side loading guide wire gripping device as disclosed in U.S. Pat. No. 4,829,999, herein incorporated by reference. Gripper 20 is molded onto stopcock 25 at its proximal end. Stopcock 25 has a fluid port 22 adapted to receive a syringe and a valve 26 that directs fluid flow. Valve 26 may be aligned to make a fluid path between port 22 and gripper 20, between the gripper 20 and the pressure transducer 30, or to a closed position. Stopcock 25 can be made of any medical grade, non-compressible material and is preferably made of polycarbonate. FIG. 3b is an end view of gripper 20.

Figure 3C:
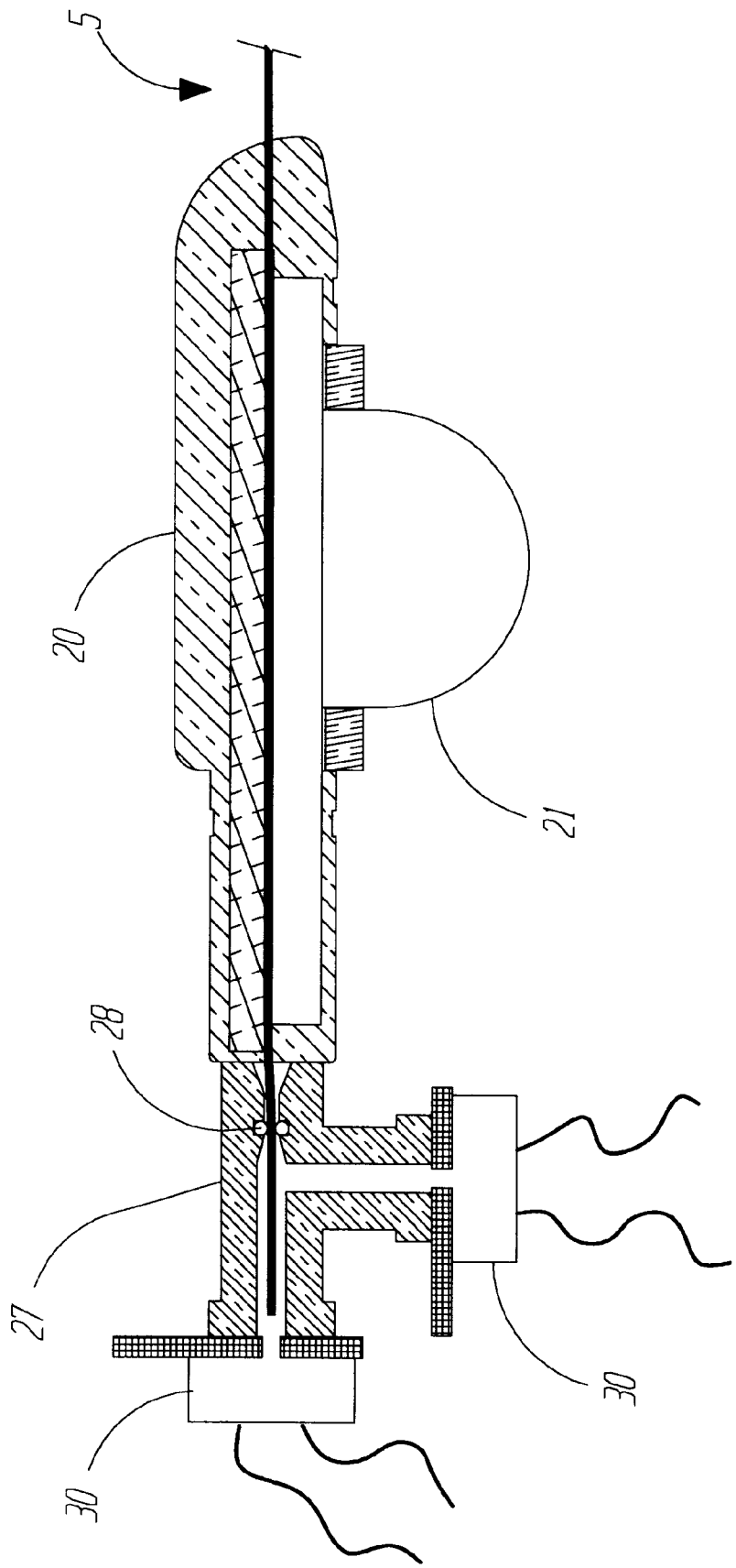
FIG. 3c is a side view of another embodiment of a connector assembly for use with the invention.

In FIG. 3c a gripper 20 like that of the previous embodiment is molded onto a connector 27. Connector 27 has three ports. The first and second ports are attached to pressure transducers 30. The third port is attached to gripper 20. Within the third port is a neoprene o-ring 28 that provides a fluid tight seal capable of holding a pressurized liquid or gel within connector 27. Examples of these liquids or gels include water, saline, silicone oil, silicone gel, alcohol, or perfluorocarbon. When elongate body 5 is inserted into connector 27 it passes through the o-ring 28 and creates a fluid communication path between the pressure transducers 30 and lumen 11 of elongate body 5.

In use either of the connector assemblies shown in FIGS. 3a and 3c could be used with either of the tip configurations shown in FIGS. 2a–2d. However, the actual method of use for each configuration will vary depending on the choice of connector assembly. Use of the connector assembly of FIG. 3a and 3b requires the compression of finger pads 21, thereby opening a channel in gripper 20. The core member 6 may then be laid in the channel and then slid into stopcock 25. Finger pads 21 may then be released, thereby securing the hypotube within stopcock 25. The elongate body 5 may then be positively prepped by orienting the valve 26 such that there is a fluid path between the lumen 11 and port 22. A syringe may be fitted into port 22 and fluid injected until all air is forced through holes 15. Valve 26 may then be oriented such that there is a fluid path between holes 15 and the pressure transducer 30. This embodiment would then be used like a standard guide wire.

Use of the connector assembly of FIG. 3c requires that the elongate body 5 be positively prepped by injecting a fluid into the proximal end of lumen 11 until all air is expelled from holes 15. The guide wire may then be used like any other guide wire. When the guide wire is located in a position where it is desired to measure pressure, the prefilled connector assembly of FIG. 3c is attached to the proximal end of the core member 6. Compression of finger pads 21 opens a channel in gripper 20. The core member 6 may then be laid in the channel slid through o-ring 28 and into connector 27. Finger pads 21 may then be released, thereby securing the hypotube within connector 27. When transducers 30 are connected to circuitry as describe for a dual sensor system, a pressure measurement can be taken.

Figure 4:
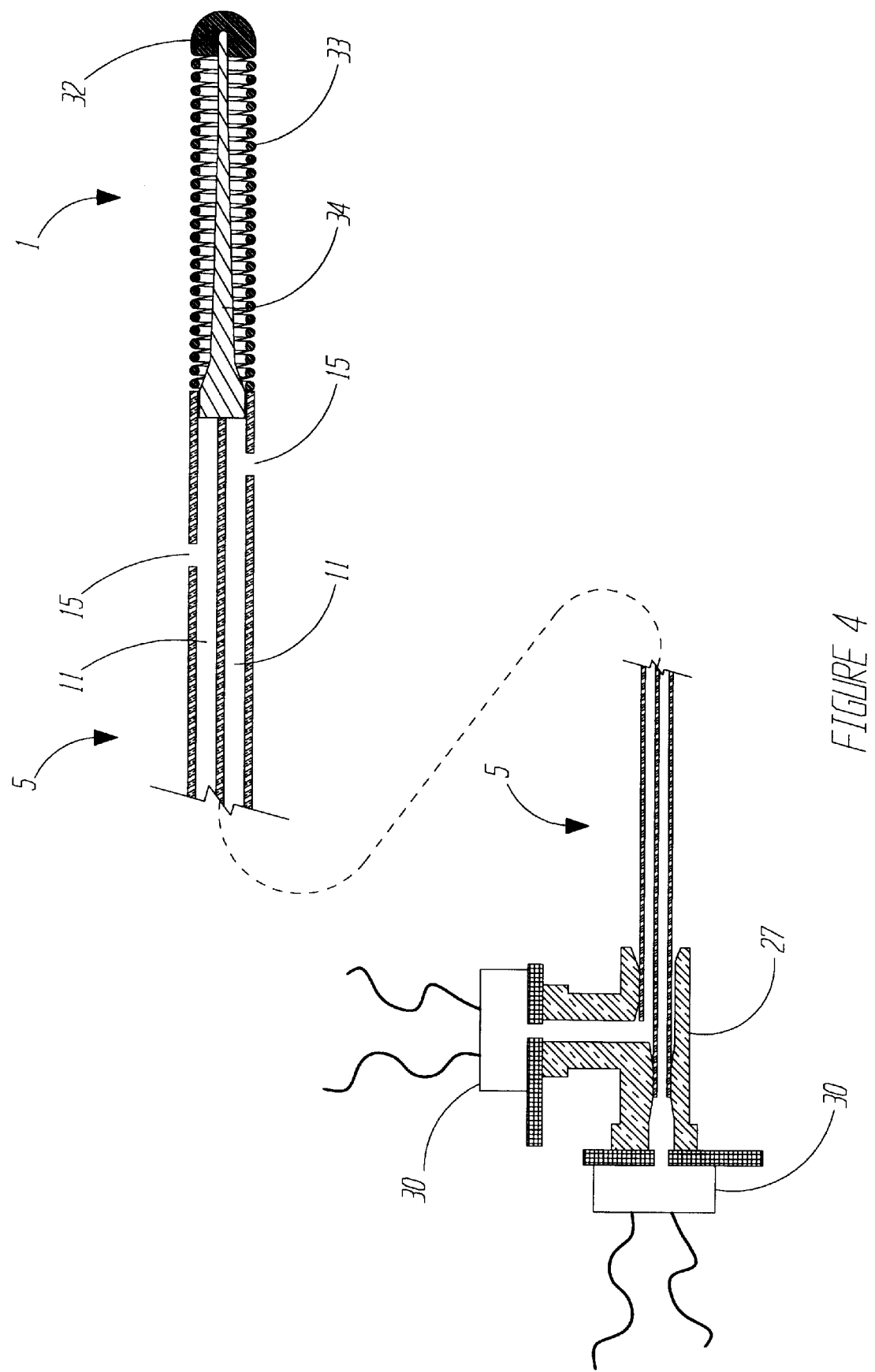
FIG. 4a is a cross section of a second embodiment of the invention.

FIG. 4 shows an embodiment of the invention with more than one lumen. This embodiment also may have an atraumatic tip 1, as previously described, attached to the distal end of an elongate body 5. Elongate body 5 may be 150–300 cm in length. Elongate body 5 is shown in FIG. 4 as having two lumens 11 but may have more than two lumens. Each lumen 11 is in fluid communication with a separate set of holes 15, as previously described. Each set of holes 15 is longitudinally displaced relative to the other sets of holes 15. Longitudinal displacement of each set of holes 15 allows pressure to be measured in multiple locations within the vasculature simultaneously. Each set of holes 15 is in fluid communication, via lumen 11, with a transducer 30, as previously described. Each lumen 11 is formed by a surrounding non-compliant material like stainless steel, polyimide, a polyimide composite, Nitinol ™, or other suitable medical grade metal or polymer. At the proximal end of elongate body 5 there is a connector 27 which is removeably attached to elongate body 5. Alternatively, the embodiment of FIG. 4 may also include membrane sleeves 16 covering holes 15 (not shown).

In use, the embodiment of FIG. 4 would be prepped be flushing a non-compliant liquid or gel through lumens 11 until all air has been expelled from through holes 15. The device can then be advanced through a patient's vasculature to a point where it is desired to measure pressure. As an example, the device could be advance until the distal set of holes 15 is on the distal side of a vascular lesion. This would leave the proximal set of holes 15 on the proximal side of a lesion. Connector 27 may then be fit onto the proximal end of the device such that each lumen 11 is in fluid communication with a pressure transducer 30. In the example, pressure could then be measured on each side of the lesion. This information will give the users of the device a pressure gradient across the lesion and another tool in determining the extent of the occlusion.

In addition to the methods of use previously described, those skilled in the art will appreciated that in any body lumen where pressure measurement is desired or where guide wires are used such as, gastrointestinal, neurological, spinal, urological, respiratory or in the peripheral vasculature. Further, while the specification describes the preferred designs, materials, methods of manufacture and methods of use, those skilled in the art will appreciate the scope and spirit of the invention with reference to the appended claims.

I claim:

1. A medical guidewire comprising:
   an elongate body having a proximal end, a distal end, a lumen extending between the proximal end of the elongate body and the distal end of the elongate body, the lumen surrounded by noncompliant material, and at least one hole near the distal end of the elongate body to provide pressure communication between the lumen and a pressure source external to the elongate body;
   a noncompliant connector attached to the proximal end of the elongate body in fluid communication with the lumen; and
   at least one pressure transducer adjacent the proximal end of the elongate body and directly attached to the noncompliant connector.

2. A medical guidewire as in claim 1, wherein the elongate body includes a metallic tube having a tapered distal section and a polymer coating surrounding the distal section.

3. A medical guidewire as in claim 1, wherein the elongate body comprises:
   a first metallic tube having a tapered distal section; and
   a second noncompliant tube attached to a portion of the distal section of the first metallic tube and extending distally of the first metallic tube.

4. A medical guidewire as in claim 3, wherein the first metallic tube includes stainless steel and the second noncompliant tube includes a shape memory alloy.

5. A medical guidewire as in claim 1, wherein the at least one pressure transducer is adapted to have a full scale pressure capability which is 10–10,000 times greater than the range of interest.

6. A medical guidewire as in claim 1, wherein the at least one hole is sealed by a valve which allows fluid to flow out of the lumen but not into the lumen and allows pressure to be communicated across the valve.

7. A medical guidewire as in claim 1, wherein the noncompliant connector has a first port adapted to connect to the distal end of the elongate body, a second port adapted to connect to at least one pressure transducer, and at least one additional port.

8. A method of measuring pressure changes across a vascular legion comprising:
   inserting an elongate medical pressure sensing device into the vessel, the device having a proximal end, a distal end, at least two lumens therethrough, at least two laterally displaced sets of holes near the distal end, wherein at least one set of holes provides pressure communication between each of the lumens and a pressure source exterior of the elongate medical pressure sensing device, a noncompliant connector attached to the proximal end of the elongate medical pressure sensing device in fluid communication with the lumens therein, and at least two pressure transducers attached to the noncompliant connector wherein at least one pressure transducer is in fluid communication with each lumen;
   advancing the elongate medical pressure sensing device through the vessel to a point where one set of holes is distal of the lesion and another set of holes is proximal to the site; and
   then reading pressure from the distal side of the lesion and the proximal side of the lesion simultaneously.

9. An elongate medical device comprising:
   an elongate body having a proximal end, a distal end, a lumen extending between the proximal end of the elongate body and the distal end of the elongate body, the lumen surrounded by noncompliant material, and at least one hole near the distal end of the elongate body to provide pressure communication between the lumen and a pressure source external to the elongate body;
   a noncompliant connector attached to the proximal end of the elongate body in fluid communication with the non-compliant lumen;
   at least one pressure transducer adjacent the proximal end of the elongate body and directly attached to the noncompliant connector; and
   a one way valve which allows fluid to flow out of the at least one hole but not into the at least one hole and allows pressure to be communicated across the valve.

* * * * *